United States Patent [19]

Cook et al.

[11] Patent Number: 5,725,873
[45] Date of Patent: Mar. 10, 1998

US005725873A

[54] METHOD OF IMPROVING THE GROWTH OR THE EFFICIENCY OF FEED CONVERSION OF AN ANIMAL AND COMPOSITIONS FOR USE THEREIN

[75] Inventors: Mark E. Cook, Madison; Daria L. Jerome, Middleton, both of Wis.

[73] Assignee: Wisconsin Alumni Research Foundation, Madison, Wis.

[21] Appl. No.: 684,785

[22] Filed: Jul. 22, 1996

[51] Int. Cl.[6] .............. C09D 191/00; A61K 39/395; A23K 1/16; C07K 16/26

[52] U.S. Cl. .............. 424/442; 424/283.1; 530/388.85; 530/389.1; 530/388.24; 426/92; 426/89; 426/140; 106/148.1; 106/147.3; 106/243

[58] Field of Search .............. 530/389.4, 389.5, 530/390.1, 389.1, 388.85, 388.24; 424/442, 157.1, 158.1, 164.1, 283.1; 106/147.3, 148.1, 243; 426/92, 89, 140

[56] References Cited

U.S. PATENT DOCUMENTS

| | | |
|---|---|---|
| 3,119,691 | 1/1964 | Ludington et al. .............. 99/2 |
| 4,357,272 | 11/1982 | Polson . |
| 4,550,019 | 10/1985 | Polson . |
| 4,748,018 | 5/1988 | Stolle et al. . |
| 5,080,895 | 1/1992 | Tokoro . |
| 5,428,072 | 6/1995 | Cook et al. .............. 514/560 |

FOREIGN PATENT DOCUMENTS

| | | |
|---|---|---|
| 0231817A2 | 8/1987 | European Pat. Off. . |
| 0241441A1 | 10/1987 | European Pat. Off. . |
| 0426463A2 | 5/1991 | European Pat. Off. . |
| WO9101803 | 2/1991 | WIPO . |
| 0556883A1 | 8/1993 | WIPO . |
| WO9421284 | 9/1994 | WIPO . |
| WO9604933 | 2/1996 | WIPO . |
| 0707798A1 | 4/1996 | WIPO . |
| WO9622028 | 7/1996 | WIPO . |

OTHER PUBLICATIONS

Albright, RB et al. Drug. Dev. Ind. Pharm. 20(12):2035–2039, Jul. 1994.

*Primary Examiner*—David Saunders
*Assistant Examiner*—F. Pierre Vander Vegt
*Attorney, Agent, or Firm*—Quarles & Brady

[57] ABSTRACT

A method of improving the efficiency of an animal to convert feed into desirable body tissue involves feeding the animal feed particles having an inner core of nutrients and an outer layer of fat containing antibodies which can protect the animal from contacting diseases that can adversely affect the animal's ability to grow or efficiently convert its feed into body tissue.

1 Claim, No Drawings

METHOD OF IMPROVING THE GROWTH OR THE EFFICIENCY OF FEED CONVERSION OF AN ANIMAL AND COMPOSITIONS FOR USE THEREIN

FIELD OF THE INVENTION

The present invention relates generally to the feeding of animals. More particularly, it relates to a method of improving the animal's growth or the efficiency of the animal to convert its feed into desirable body tissue (e.g. muscle) and compositions for use in the method.

BACKGROUND OF THE INVENTION

It is known that healthy, disease-free animals grow faster or are more able to convert their feed efficiently into body tissue than sick or immune-challenged animals. Obviously, faster growth or a more efficient conversion of feed into desirable body tissue in an animal is both economically and ecologically important, especially in animals raised for food. For this, and other reasons, it is desirable to prevent animals from contacting diseases.

One approach to keeping animals healthy is to give the animals antibiotics. However, that approach is not desirable for animals raised for food because there can be antibiotic residues in the food.

Another approach to keeping animals healthy is to immunize the animals. This can be done by vaccinating the animals against specific diseases to produce an active immunization or by administering to the animals antibodies to produce a passive immunization.

In U.S. Pat. Nos. 4,748,018 and 5,080,895, methods are disclosed for passively immunizing animals against intestinal diseases which could interfere with the animal's efficient conversion of feed. The patented methods basically comprise orally administering to said animals effective amounts of egg-derived materials containing avian antibodies which are obtained by immunizing egg-laying hens with specific antigens which will produce such antibodies, and obtaining the antibody containing material from eggs laid by the hen. In both patents, the antibody containing egg materials are reduced to powders and fed to the animals to be passively immunized.

BRIEF SUMMARY OF THE INVENTION

It is the primary object of the present invention to disclose a novel method to improve the animals growth or the efficiency of the animal to convert its feed into desirable body tissue.

Another object of the invention is to disclose an animal feed for animals for use in the inventive method.

The method of the present invention to improve the animals growth or the efficiency of the animal to convert its feed into desirable body tissue comprises orally administering to said animal feed particles having an inner core comprising primarily non-fat nutrients and an outer layer of fat which contains a safe and effective amount of antibodies that help protect the animal from disease or other antigens that can adversely affect the animal's growth or the efficiency of the animal to convert feed into desirable body tissue.

The compositions of the present invention are animal feed particles having an inner core comprised of nutrients, such as proteins and carbohydrates, and an outer layer of fat that contains the antibodies encapsulated therein.

The compositions of the present invention are conveniently made by first forming a nutrient mixture to produce an inner core, and then coating the outer surface of the core with a layer of fat containing antibodies encapsulated therein so the antibody is stabilized and substantially protected against antibody destroying factors, such as environmental conditions and intestinal proteases.

In an especially preferred embodiment of the invention, the antibodies in the fat are obtained from the egg of a hen which has been injected with an antigen that results in the production by the hen of those antibodies.

The compositions of the present invention are superior to previously known animal feeds in which antibody-containing powders were mixed with nutrients, including fat, and then granulated or extruded because the fat layer in the method of the present invention is applied to the core after the pelletization, extrusion, granulation or expansion process. As a result the antibodies in the outer fat layer of the compositions of the present invention are not degraded by the elevated temperatures that can arise during the pelletization, granulation, extrusion or expansion process. The compositions of the present invention are also superior to prior art feeds because the outer layer of fat in which the antibodies are encapsulated helps protect the antibodies from stomach acid and intestinal enzymes.

DESCRIPTION OF THE PREFERRED EMBODIMENT

In the preferred embodiment of the present invention, the animal feed particles comprise an extruded inner core which contains primarily the desired non-fat materials, such as proteins and carbohydrates, and an outer layer of fat which contains the antibodies encapsulated therein. The outer layer also can contain other ingredients, such as oil soluble vitamins and the inner core can, of course, also contain fat, if desired.

In the preferred practice of the method of invention, the animal feed with the antibody-containing outer layer is orally fed to the animal in an amount which will passively immunize the animal.

The antibodies for use in the present invention are those which can alter physiological processes that adversely affect growth and feed efficiency. They can be antibodies that are against diseases or specific endogenous regulators of food intake and gastrointestinal motility. The antibodies are preferably derived from the eggs of hens which have been previously immunized to produce those antibodies as described in U.S. Pat. No. 4,748,018 or U.S. Pat. No. 5,080,895. Especially preferred as the antibody-containing material are spray dried egg yolks and whole eggs. However, other non-egg derived antibody-containing materials may be used.

The preferred inner core for the animal feed particles is an extrusion which contains a mixture of nutrients, such as grains, with or without added sugars, carbohydrates and/or proteins. The core will normally contain less than the desired total amount of the dietary fat for the animal because of the fat in the outer layer.

The fat for use in the outer layer to encapsulate and protect the antibody can be any fat or lipid, which can be readily mixed with the antibody containing material to form a mixture, which contains the antibody encapsulated therein and which can be readily sprayed or otherwise coated on the outer surface of the core. Especially preferred are those fats which are solid at ambient temperatures and which will protect the antibodies from adverse environmental conditions and intestinal enzymes. Especially preferred as the fat is a mixture of tallow and conjugated linoleic acid (CLA) which also is known to increase feed efficiency.

Representative of other fats that can be used are the following:

Lard

Yellow Grease

Poultry Fat

Spent Restaurant Oil

Animal Oils

Vegetable Oils

Fish Oils

Oil Derivatives, i.e., lecithin and

Mixtures thereof.

The practice of the present invention is further illustrated by the following examples:

EXAMPLE 1

Preparation Of Antibodies.

An antigen, such as cholecystokinin peptide which produces cholecystokinin (CCK) antibodies, is injected intramuscularly into mature hens at a dose of about 50 mg to 1000 mg with a water-in-oil emulsion adjuvant. Samples of the whole eggs or yolks of eggs from the hens are assayed by known methods for CCK antibody content. When the CCK antibody titer reaches a maximum level, the whole eggs or yolks of eggs are collected and pooled, homogenized and spray dried to obtain a powder.

EXAMPLE 2

Preparation Of Animal Feed Particles With Outer Layer Of Fat Containing Antibodies.

A CCK antibody-containing powder made by the process of Example 1 is mixed with tallow to form a blend in which the powder is substantially encapsulated by the fat. The fat mixture is then spray coated upon inner cores made by the pelletization, the granulation, the extrusion or the expansion of a plasticized mixture of nutrients, including carbohydrate, protein and water. The resulting animal feed particles have an inner core of nutrients and an outer layer of fat containing CCK antibodies.

EXAMPLE 3

Animal Feeding Test.

Ducks are fed the animal feed of Example 2 and their biological responses are determined. It is found that the ducks receiving the animal feed of Example 2 demonstrate an improved body weight gain and a more efficient rate of feed conversion than control ducks.

Table 1 shows the results obtained in 14 day old ducks fed a control feed and an otherwise identical feed (BRAVO) having an outer antibody-containing layer.

TABLE 1

| | | | (Lbs) |
|---|---|---|---|
| | ABOVE BODY WEIGHT SUMMARY | | |
| TREATMENT | 14 day weight | 27 day weight | 14–27 day gain |
| Control | 1.45 | 4.48 | 3.02 |
| Bravo | 1.39 | 4.32 | 2.93 |
| TREATMENT | 39 day weight | 14–39 day gain | |
| Control | 6.93 | 5.48 | |
| Bravo | 7.11 | 5.72 | |
| | FEED CONVERSION DATA | | |
| Treatment | 14–27 feed/bird | 0–27 feed/bw* | 14–17 feed/gain |
| Control | 5.50 | 1.229 | 1.819 |
| Bravo | 5.16 | 1.192 | 1.758 |
| Treatment | 14–39 feed/bird | 0–39 feed/bw* | 14–39 feed/gain |
| Control | 11.783 | 1.720 | 2.170 |
| Bravo | 10.859 | 1.530 | 1.904 |

*bw = body weight

It will be apparent to those skilled in the art that the present invention can be used to prepare the animal feed for a wide variety of food animals, including without limitation, ducks, chickens and turkeys.

It also will be readily apparent to those skilled in the art that a large number of changes and modifications can be made without departing from the spirit and scope of the present invention. Therefore, it is intended that the invention only be limited by the claims which follow.

We claim:

1. A particulate animal feed comprising an inner core of nutrients containing carbohydrates and proteins and an outer layer of an edible fat having cholecystokinin (CCK) antibodies encapsulated therein.

* * * * *